US00RE38839E

(19) United States
(12) Reissued Patent
Magnante

(10) Patent Number: US RE38,839 E
(45) Date of Reissued Patent: Oct. 18, 2005

(54) METHODS AND DEVICES TO DESIGN AND FABRICATE SURFACES ON CONTACT LENSES AND ON CORNEAL TISSUE THAT CORRECT THE EYE'S OPTICAL ABERRATIONS

(76) Inventor: Peter C. Magnante, 218 Wigwom Rd., West Brookfield, MA (US) 01585

(21) Appl. No.: 10/192,104

(22) Filed: Jul. 10, 2002

Related U.S. Patent Documents

Reissue of:
(64) Patent No.: 6,086,204
Issued: Jul. 11, 2000
Appl. No.: 09/399,022
Filed: Sep. 20, 1999

(51) Int. Cl.[7] ..... A61B 3/10
(52) U.S. Cl. ..... 351/212; 219/121.75
(58) Field of Search ..... 351/205, 211, 351/212, 219, 221, 246, 160 R, 176, 177; 606/4, 5; 219/121.6, 121.61, 121.69, 121.75

(56) References Cited

U.S. PATENT DOCUMENTS

| | | | |
|---|---|---|---|
| 4,702,576 | A | 10/1987 | Magnante |
| 4,993,827 | A | 2/1991 | Benedek et al. |
| 5,068,514 | A | 11/1991 | Lunney |
| 5,396,045 | A | 3/1995 | Opdyke |
| 5,579,063 | A | 11/1996 | Magnante et al. |
| 5,777,719 | A | 7/1998 | Williams et al. |
| 5,861,114 | A | 1/1999 | Roffman et al. |
| 5,949,521 | A | 9/1999 | Williams et al. |
| 6,033,075 | A | 3/2000 | Fujieda et al. |
| 6,082,856 | A | 7/2000 | Dunn et al. |
| 6,095,651 | A | 8/2000 | Williams et al. |
| 6,244,708 | B1 | 6/2001 | Chapman et al. |
| 6,271,914 | B1 | 8/2001 | Frey et al. |
| 6,271,915 | B1 | 8/2001 | Frey et al. |

OTHER PUBLICATIONS

"Aberration–Correcting Contact Lenses to Improve Human Vision", Peter C. Magnante, Nancy J. Coletta, and Bruce D. Moore, Brookfield Optical Systems, West Brookfield, MA 01585, New England College of Optometry, Boston, MA 02115.

"Plastic Optics" by Richard F. Weeks, Sep. 1975, Optic News, pp. 5–11.

International Search Report, Application No. PCT/USOO/22466.

*Primary Examiner*—George Manuel
(74) *Attorney, Agent, or Firm*—Robert F.I. Conte; Barnes & Thornburg

(57) ABSTRACT

Methods and devices are described that are needed to design and fabricate modified surfaces on contact lenses or on corneal tissue that correct the eye's optical aberrations beyond defocus and astigmatism. The invention provides the means for: 1) measuring the eye's optical aberrations either with or without a contact lens in place on the cornea, 2) performing a mathematical analysis on the eye's optical aberrations in order to design a modified surface shape for the original contact lens or cornea that will correct the optical aberrations, 3) fabricating the aberration-correcting surface on a contact lens by diamond point turning, three dimensional contour cutting, laser ablation, thermal molding, photolithography, thin film deposition, or surface chemistry alteration, and 4) fabricating the aberration-correcting surface on a cornea by laser ablation.

26 Claims, 7 Drawing Sheets

Figure 1:
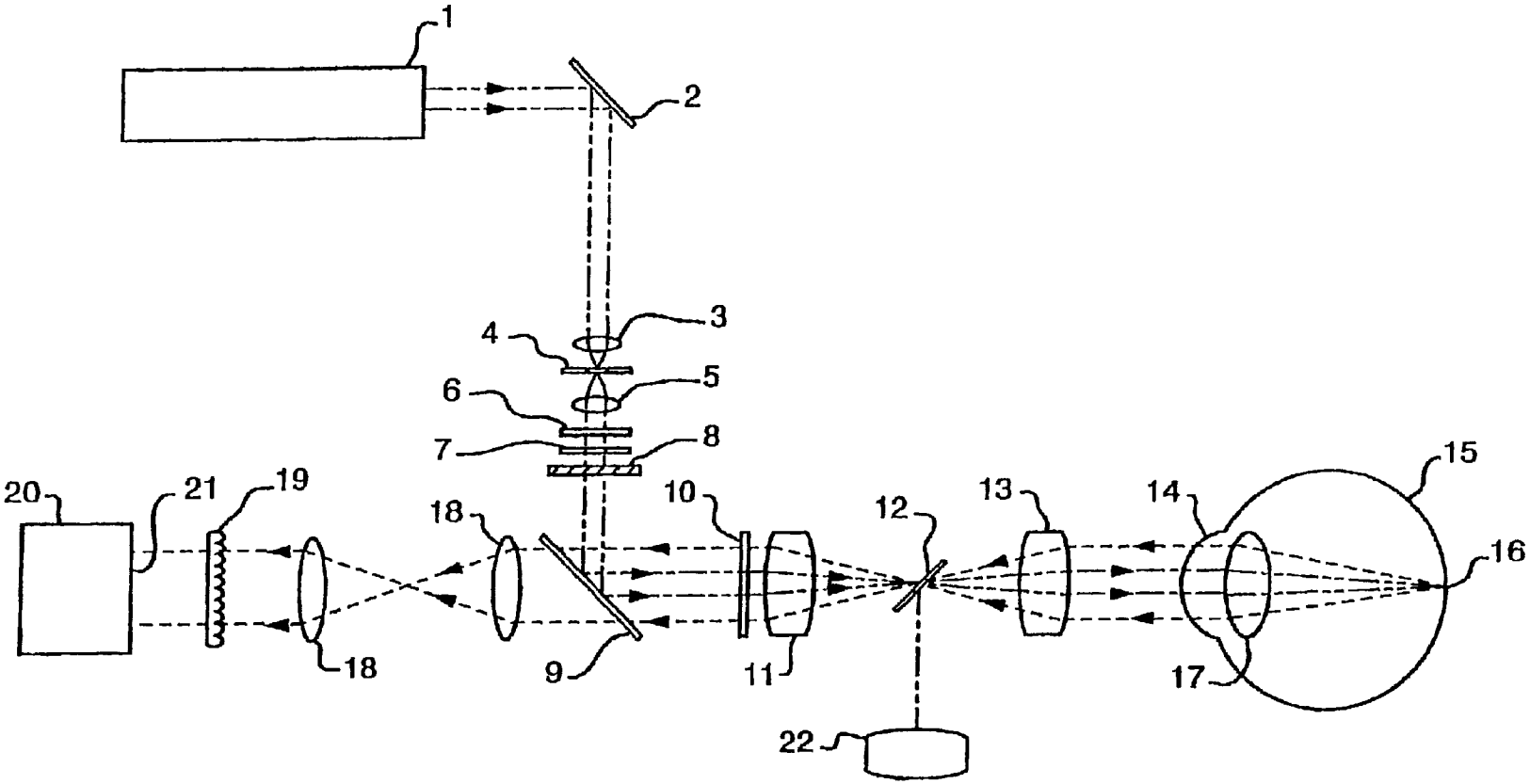

| UNIT VECTOR | REPRESENTING |
|---|---|
| A | INCIDENT RAY |
| B | REFRACTED RAY |
| N | NORMAL TO SURFACE |
| T | TANGENT TO SURFACE AND COPLANAR WITH A & B |

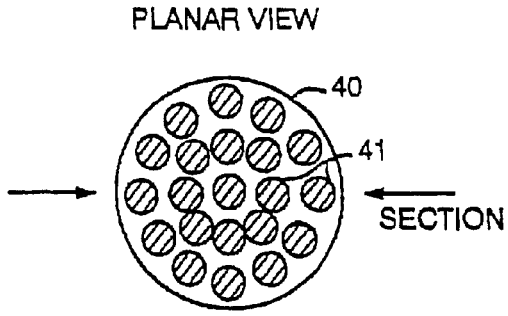

TOP SURFACE OF MECHANICAL "FINGERS" SHOWN AS CROSSHATCHED CIRCLES. THE NUMBER SHOWN IS APPROXIMATE. THE AREA OF THE ARRAY IS TO COVER THE SURFACE OF THE LENS.

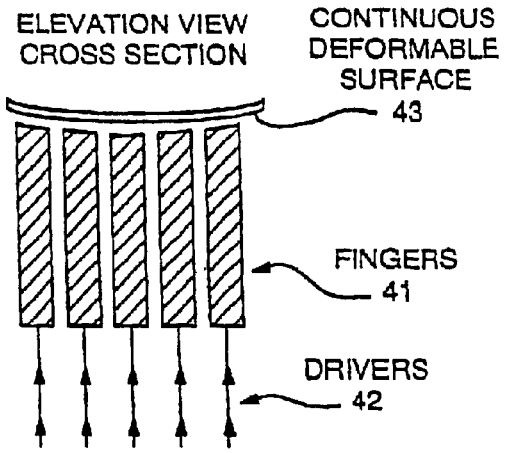

MECHNICAL "FINGERS" DRIVEN BY ELECTROMECHANICAL DRIVERS (E.G. PIEZOELECTRIC LINEAR TRANSDUCERS)

SEGMENTED DIE FOR MECHANICAL FORCE THERMAL MOLDING:
1) CLOSE PACKED ARRAY OF MECHANICAL "FINGERS" WITH SURFACE CURVATURE MATCHING THAT OF THE LENS BLANK'S BASE CURVATURE, AND 2) ELECTROMECHANICAL DRIVERS FOR MICROMETER DISPLACEMENT OF INDIVIDUAL "FINGERS" TO MATCH LENS SURFACE PRESCRIPTION.

FIG. 7

METHODS AND DEVICES TO DESIGN AND FABRICATE SURFACES ON CONTACT LENSES AND ON CORNEAL TISSUE THAT CORRECT THE EYE'S OPTICAL ABERRATIONS

Matter enclosed in heavy brackets [ ] appears in the original patent but forms no part of this reissue specification; matter printed in italics indicates the additions made by reissue.

1. BACKGROUND OF THE INVENTION

1.1 Measurements of the Eye's Aberrations

There are several objective optical techniques that have been used to measure the wavefront aberrations of the eye. The aberroscope, which is disclosed by Walsh et al. in the Journal of the Optical Society of America A, Vol.1, pp. 987–992 (1984), projects a nearly collimated beam into the eye which is spatially modulated near the pupil by a regular grid pattern. This beam images onto the retina as a small bright disk which is modulated by the dark lines of the grid pattern. Since the eye's pupillary aberrations distort the retinal image of the grid pattern, measurements of the distortions on the retina reveal the pupillary aberrations.

The spatially resolved refractometer, which is disclosed by Webb et al. in Applied Optics, Vol. 31, pp. 3678–3686 (1992), projects a small diameter collimated beam through the eye's pupil. Instead of being spatially modulated by a physical grid as with the aberroscope, the spatially resolved refractometer's beam is raster-scanned across the entire pupil. A sequence of retinal images of the focused light is recorded with each image associated with a particular location at the pupil. A mapping of the relative locations of these retinal images reveals the aberrations across the pupil.

Analyzers of retinal point-spread functions have been disclosed by Artal et al. in the Journal of the Optical Society of America A, Vol. 5, pp. 1201–1206 (1988). Analyzers of retinal line-spread functions have been disclosed by Magnante et al. in Vision Science and Its Applications, Technical Digest Series (Optical Society of America, Washington, D.C.), pp. 76–79 (1997). When used to measure the wavefront aberrations of the eye, these spread function analyzers project a small diameter circular beam into the eye at the center of the pupil. This beam focuses onto the retina as a tiny source of light. The light from this tiny retinal source scatters back through the dilated pupil. A small circular aperture (approximately 1 mm diameter) in the imaging section of the analyzer is located conjugate to the pupil plane. This aperture may be translated up/down or side/side to sample specific regions in the pupil plane where wavefront aberration measurements are sought. An imaging lens focuses the light through the small aperture onto the imaging plane of a camera. Measurements of the relative locations of the focal spots for the various locations of the small aperture characterize the pupillary wavefront aberrations.

The Hartmann-Shack wavefront sensor for ordinary lens or mirror testing was disclosed originally by Shack et al. in the Journal of the Optical Society of America, Vol. 61, p. 656 (1971). This type of wavefront sensor was adapted to measure the wavefront aberrations of the eye by Liang et al., Journal of the Optical Society of America A, Vol. 11, pp. 1949–1957 (1994). The Hartmann-Shack wavefront sensor is similar to point-spread (or line-spread) function analyzers in that: 1) it projects a fine point of light onto the retina through a small diameter pupil of the eye, and 2) the light which is scattered back from the retina through the eye's pupil is imaged onto a camera with a lens that is conjugate to the eye's pupil. However, instead of using a single lens with a moveable small aperture to image the retinal image onto the camera, the Hartmann-Shack wavefront sensor utilizes a regular two-dimensional array of small lenses (commonly called a microlens array) which is optically conjugate to the eye's pupil to focus the back scattered light from the retinal image onto the camera. Typical diameters of individual microlenses range from 0.1 to 1.0 millimeter. With the Hartmann-Shack wavefront sensor, instead of having a single spot of light corresponding to a single aperture imaged by the camera, there is an array of focused spots imaged by the camera . . . one spot for each lens in the microlens array. Furthermore, each imaged spot of light corresponds to a specific location at the eye's pupil. Measurements of the locations of the array of imaged spots are used to quantify the pupillary aberrations.

Measurements of the wavefront aberrations of the eye to a high degree of precision using an improved Hartmann-Shack wavefront sensor are described in 1998 U.S. Pat. No. 5,777,719 to Williams and Liang. What is described in U.S. Pat. No. 5,777,719 improves upon what was described previously by Liang et al. in the Journal of the Optical Society of America A, Vol. 11, pp. 1949–1957 (1994). Device improvements described in the Williams and Liang 1998 Patent include: 1) a wavefront correcting deformable mirror, 2) a method to feedback signals to the deformable mirror to correct the wavefront aberrations, and 3) a polarizer used with a polarizing beamsplitter to reduce unwanted stray light from impinging on the recording camera.

Although the precision of the resulting wavefront aberration measurements cited by Williams and Liang is impressive, the implementation of a deformable mirror and a feedback loop is very costly and is not necessary for achieving the purposes of my invention.

Furthermore, the polarizer with polarizing beamsplitter cited in the Williams and Liang patent are not necessary for achieving the purposes of my invention, and those devices are replaced in my invention with a single device called an optical isolator (consisting of a polarizer fused to a quarter-wave plate). The optical isolator achieves the same purpose as the pair of polarizing devices described by Williams and Liang, namely reducing unwanted stray light.

Finally, a laser is cited as the preferred illumination source in the Williams and Liang patent. However, a conventional laser is improved upon in my invention through the use of a diode laser operated below threshold. Such a light source is not as coherent as a standard laser operating above threshold, Images formed with such a non-coherent source are less granular (having less "speckle") than those formed by coherent sources. This improvement results in less noisy granularity in the microlens images and, thereby, improves the accuracy of the image processing which depends on precisely locating the microlens images.

1.2 Analysis of Hartmann-Shack Wavefront Sensor Data to Characterize the Eye's Optical Aberrations The essential data provided by a Hartmann-Shack wavefront sensor modified to measure the human eye are the directions of the optical rays emerging through the eye's pupil. The method of deriving a mathematical expression for the wavefront from this directional ray information is described by Liang et al. in the Journal of the Optical Society of America A, Vol. 11, pp. 1949–1957 (1994). It is also the method cited in 1998 U.S. Pat. No. 5,777,719 to Williams and Liang. First, the wavefront is expressed as a series of Zernike polynomials with each term weighted initially by an unknown coefficient. Zernike polynomials are described in Appendix 2 of "Optical Shop Testing" by D. Malacara (John Wiley and Sons, New York, 1978). Next, partial derivatives (in x & y) are then calculated from the Zernike series expansion. Then, these partial derivative expressions respectively are set equal to the measured wavefront slopes in the x and y directions obtained from the wavefront sensor measurements. Finally, the method of least-squares fitting of polynomial series to the experimental wavefront slope data is employed which results in a matrix expression which, when solved, yields the coefficients of the Zernike polynomials. Consequently, the wavefront, expressed by the Zernike polynomial series, is completely and numerically determined numerically at all points in the pupil plane. The least-squares fitting method is discussed in Chapter 9, Section 11 of "Mathematics of Physics and Modern Engineering" by Sokolnikoff and Redheffer (McGraw-Hill, New York, 1958).

Although the above described methods to calculate the aberrated wavefront of the eye are cited in the Williams and Liang patent, it is significant to note that there is not any description in their patent of how to design an aberration-correcting contact lens or corneal surface from the aberrated wavefront data. These details for designing an aberration-correcting contact lens or corneal surface are not obvious, and require a number of complex mathematical steps. These mathematical details for designing aberration correcting surfaces on contact lenses or on the cornea itself are described fully in my invention.

Furthermore, Williams and Liang demonstrate that the eye's aberrations can be corrected by properly modifying the surface of a reflecting mirror. However, they do not demonstrate or provide any description of how aberration-correcting surfaces can be designed on refractive surfaces such as those on contact lenses or on the cornea itself. My invention gives a detailed mathematical description of how to design such refracting optical surfaces that correct the eye's aberrations.

1.3 Fabrication of Conventional Contact Lenses

Conventional contact lenses with spherical or toroidal surface contours are made routinely using a method called single point diamond turning which utilizes very precise vibration-free lathes. The contact lens blank rotates on a spindle while a diamond point tool, moving along a precise path, cuts the desired surface contour. The end result is a surface which does not need additional polishing, and exhibits excellent optical qualities in both figure accuracy and surface finish. Figure accuracy over the lens surface is better than one wavelength of light. Surface finish, which is reported as rms surface roughness, is better than 1 microinch. Machines of this type and their use are described by Plummer et al. in the Proceedings of the 8th International Precision Engineering Seminar (American Society of Precision Engineering, pp. 24–29, 1995).

1.4 Corneal Tissue Ablation to Correct Vision

With the advent of the excimer laser, the means are available for refractive surgeons to flatten and reshape the surface of the cornea in order to improve vision. The excimer laser selectively removes microscopic layers of corneal tissue allowing light rays to focus more sharply on the retina. In the procedure known as photorefractive keratectomy (PRK), the laser ablates tissue on the surface of the cornea. In the procedure known as laser in-situ keratomileusis (LASIK), the surgeon first creates a flap on the cornea and then uses the laser to reshape tissue below the corneal surface. Layers of tissue as thin as 0.25 microns can be ablated.

With current laser procedures, it is possible only to correct relatively coarse or low order aberrations of the eye, namely high levels of nearsightedness, and moderate amounts of farsightedness and astigmatism. With the analytical methods of my invention, which take into account the corneal shape, and both the low order and higher order aberrations of the eye, a modified corneal shape is found which allows all rays from external point objects to focus sharply on the retina. By the means offered by my invention, refractive surgery procedures to improve vision will be improved greatly.

2. SUMMARY OF INVENTION

Conventional spectacles and contact lenses are able to correct the visual acuity of most people to 20/20 or better. For these individuals, the most significant refractive errors are those caused by the so-called lowest order optical aberrations, namely defocus, astigmatism and prism. However, there are many people with normal retinal function and clear ocular media who cannot be refracted to 20/20 acuity with conventional ophthalmic lenses because their corneal surfaces are extraordinarily irregular. In this group are patients with severe irregular astigmatism, keratoconus, corneal dystrophies, post penetrating keratoplasty, scarring from ulcerative keratitis, corneal trauma with and without surgical repair, and sub-optimal outcome following refractive surgery. The eyes of these people have abnormal amounts of higher order or irregular optical aberrations. An objective of the invention is to improve the vision of these patients. A further objective is to provide the best vision possible to individuals with ordinary near and farsightedness and astigmatism. To achieve these objectives, methods and devices are described that are used to design and fabricate modified surfaces on contact lenses or on corneal tissue that correct the eye's optical aberrations beyond defocus and astigmatism.

The objectives of the invention are accomplished by measuring the wavefront aberrations of a subject's eye (either with or without a contact lens on the cornea) using a device that projects a small point of light on the retina near the macula, re-images the light scattered back from the retina that emerges from the pupil onto a microlens array, and records the focal spots formed from this light when it is imaged by a microlens array on the image plane of an electronic camera. The image formed on the camera is conveyed to a computer. The computer utilizes methods to determine the coordinates of the focal spots and then to calculate the wavefront slopes of rays emerging from the subject's eye.

The objectives of the invention are further accomplished by mathematical methods which analyze the wavefront slope data as well as the shape of the subject's original contact lens or corneal surface in order to design a modified surface shape for the original contact lens or cornea that corrects the aberrations. The steps in this mathematical method are: 1) determining the normal vectors to the original contact lens or corneal surface, 2) from these normal vectors and the wavefront slope data, determine the partial derivatives of the surface for the modified contact lens or corneal surface that corrects the aberrations, and 3) fitting these partial derivatives of the aberration-correcting surface with the corresponding partial derivatives of a polynomial expression that best represents the aberration-correcting surface. From these methods, a mathematical expression for the aberration-correcting surface is obtained.

The objectives of the invention are accomplished finally by providing devices and methods to fabricate the modified aberration-correcting surfaces designed by the mathematical methods described. For contact lenses, these fabrication devices and methods include those of diamond point micromachining, laser ablation, thermal molding, photolithography and etching, thin film deposition, and surface chemistry alteration. For corneal tissue resurfacing, these fabrication devices and methods are those associated with laser ablation as used with photorefractive keratectomy (PRK) and laser in-situ keratomileusis (LASIK).

The invention may be more clearly understood by reference to the following detailed description of the invention, the appended claims, and the attached drawings.

3. DESCRIPTION OF DRAWINGS

| Figure | Description |
|---|---|
| 1 | Schematic of wavefront sensor for measuring the optical aberrations of the eye |
| 2 | Detail of microlens array showing focal spots for both reference and aberrated wavefronts |
| 3 | Refraction of rays at the anterior surface of either a contact lens or a cornea showing important parameters |
| 4 | Wavefront sensor focal spot array from an aberrated wavefront (focal length of microlens array is 200 mm) |
| 5 | Wavefront sensor focal spot array from corrected wavefront (focal length of microlens array is 200 mm) |
| 6 | Schematic of diamond point turning machine for fabricating aberration-correcting contact lenses |
| 7 | Schematic of segmented die used for custom molding aberration-correcting contact lenses |

4. DETAILED DESCRIPTION OF THE INVENTION

4.1 Wavefront Sensor for Measuring the Eye's Optical Aberrations

A schematic drawing of a wavefront sensor which has been modified to measure the eye's optical aberrations is shown in FIG. 1. The design and operating principles of the subassemblies of the wavefront sensor are explained in detail below.

4.1.1 Projection System

In order to reduce bothersome "speckle" from coherence effects from conventional laser sources, non-coherent optical sources are preferred. Thus, source 1 can be anyone of the following: laser diode operating below threshold, light emitting diode, arc source, or incandescent filament lamp. The source beam is deflected by fold mirror 2, and focused by microscope objective lens 3 onto a small pinhole aperture 4 having a diameter typically in the range from 5 to 15 microns. Another lens 5 collimates the beam which next passes through polarizer 6 and then through aperture stop 7. Typically this stop restricts the beam diameter to about 2 mm or less. Following the stop is an electronic shutter 8 used to control the light exposure to the patient during measurement to about 1/10 sec. Beamsplitter 9 deviates the collimated beam by 90 degrees. The beam then passes through optical isolator 10 which consists of a quarter-wave plate and polarizer. Lens 11 forms a focused point image at the center of field stop 12 which the subject views through focusing eyepiece 13. The subject's eye 15 then images the light to a point spot on the retina 16. The field stop 12 and the optical isolator 10 both serve the important function of blocking bothersome corneal specular reflections and instrument lens reflections from reaching photo-electronic imaging device 20 such as a vidicon camera, a charge-coupled device or CCD camera, or a charge-injection device camera.

4.1.2 Camera System

Figure 2:
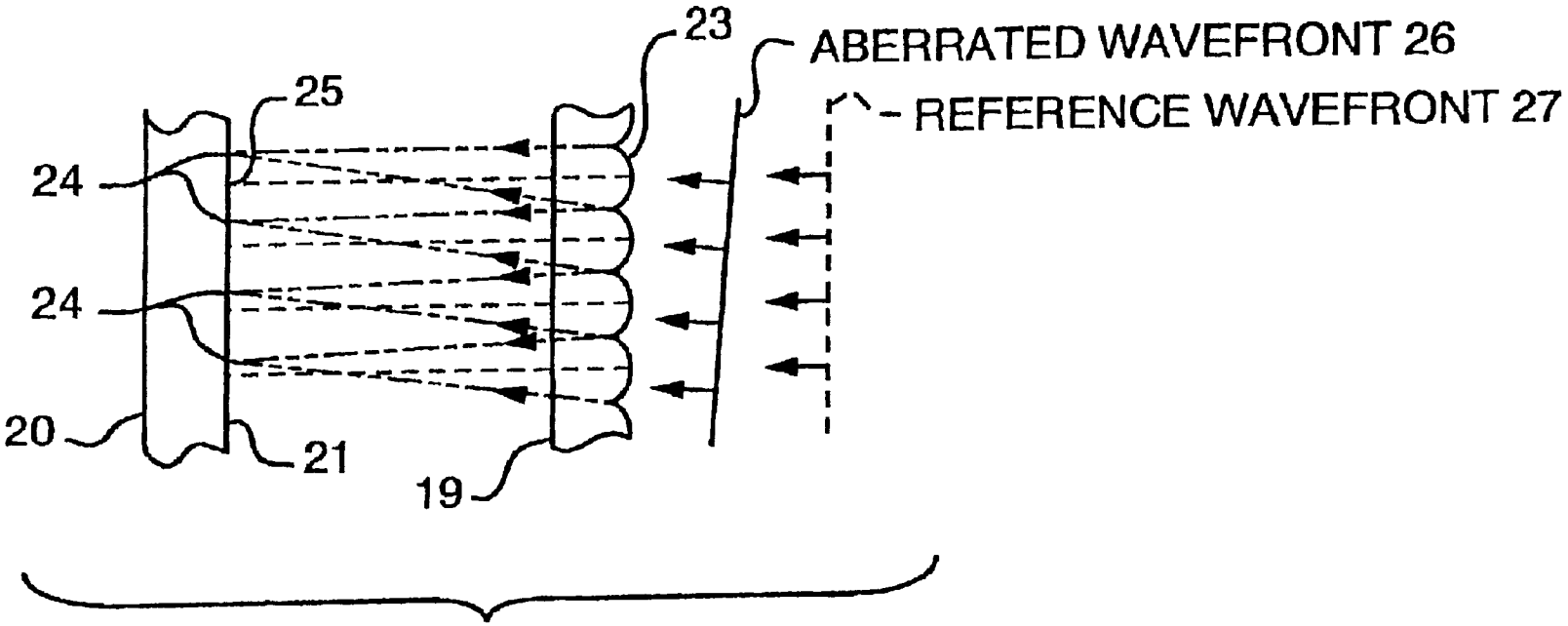

Since the retina acts as a diffuse reflector, some of the light from the retinal point image 16 is reflected back out of the eye 15 through the pupil and cornea 14. The beam emerging from the eye has its polarization randomized due to passage through the eye's birefringent cornea 14 and lens 17 as well due to scattering by the diffuse retina 16. Passing now in reverse direction through lens 13, field stop 12, lens 11, and optical isolator 10, the beam, which is now aberrated by the eye's optics, is incident from the right side onto beamsplitter 9 which transmits about half its intensity straight through to relay lens pair 18. Collectively, lenses 13, 11, and relay lens pair 18 serve to re-image subject's pupil 14 onto the plane of the microlens array 19 with unit magnification. In this way the aberrant wavefront emerging from the subject's pupil 14 is mapped exactly onto the microlens array 19. As shown in FIG. 2, each tiny lens 23 of the array images a portion of the aberrated wavefront 26 onto its focal plane 21 at or near its axis 25. The regular array of microlenses 19 produces a corresponding array of focal spots 24. Deviations of focal spots from the respective microlens axes 25 manifest the wavefront slope error over the entire surface of the microlens array (and, correspondingly, the subject's pupil). The input image plane of CCD camera 21 coincides with the focal plane 21 of the microlens array. Photo-electronic imaging device 20 interfaces with a computer equipped with a "frame-grabber" board (not shown) controlled by appropriate software. An image of the array of focal spots 24 formed by the microlens array 19 appears "live" on the computer's monitor, and is ready for "capture" by the computer when a measurement is taken.

4.1.2.1 Wavefront Slope Measurement

The nature of the wavefront slope measurement is explained now in greater detail. If a perfect plane wave is incident normally onto a perfect lens which has a small aperture near its surface, the rays passing through the aperture will be focused by the lens to the lens's focal point located on the lens's axis. Regardless of the location of the small aperture with respect to the lens surface, the imaged point will be at the same location. On the other hand, suppose the wavefront is imperfect (i.e. individual rays randomly directed and not parallel to the perfect lens's optical axis). The rays going through the small aperture now form an image at the lens's focal plane that is displaced from the lens's focal point. The displacement of the centroid of the imaged spot (between the perfect and imperfect wave measurements) divided by the distance between the lens and its focal plane (i.e. the focal length of the lens) equals the angular slope (measured in radians) of the wavefront at the location of the small aperture. Repeating this type of measurement for many locations of the small aperture over the lens surface fully characterizes the wavefront slope errors at the various measurement locations on the lens surface. In a wavefront sensor such as shown in FIG. 1, the moveable small aperture with single large diffraction-limited lens is replaced with an array of identical microlenses 19 where each one samples the wavefront at a particular location. Details of the microlens array and imaging camera used in the wavefront sensor are shown in FIG. 2. At the focal plane 21 of the microlens array 19 is the imaging surface of a photo-electronic imaging device 20 which records the locations of the focal spots 24 for all the microlenses in the array. The displacement of each focal spot 24 from the optical axis of its associated microlens 25 divided by the focal length of the microlens array equals the slope of the wavefront at the microlens's location. The locations of the optical axes of the individual microlenses are determined by a calibration procedure that involves doing a measurement when an unaberrated wavefront 27 (i.e. uniform plane wave) is incident perpendicularly onto microlens array 19. Such an unaberrated wavefront is obtained by replacing the human eye 15 shown in FIG. 1 with a diffraction-limited lens and imaging screen placed at the diffraction-limited lens's focal plane.

4.1.3 Pupil Alignment System

In FIG. 1, field stop 12 is a small hole bored in the direction of the instrument's main optical axis through a mirrored planar substrate oriented at 45 degrees. The field stop is at the focal plane of the subject's eyepiece 13. Another eyepiece 22 (called the examiner's eyepiece) is oriented at 90 degrees to the instrument's main optical axis so that the examiner can view the subject's pupil 14 by the means provided by lens 13 and the mirrored planar substrate of field stop 12. Optionally, a small video camera can be attached to examiner's eyepiece 22 so that a video image of the subject's pupil 14 can be viewed on a monitor. By either of these means, the examiner can accurately position the subject's eye 15 so that the entering beam is accurately centered with respect to the subject's pupil 14. The positioning of the subject's eye with respect to the instrument beam is controlled by a mechanism (not shown) consisting of an x-y-z translation stage that moves a chin and head rest used by the subject.

4.1.4 Data Acquisition and Processing

The subject is asked to look through eyepiece 13 at the point of light formed within field stop 12, while the examiner adjusts the location of subject's eye 15 so that the beam passes through the center of the pupil 14. Prior to taking a measurement, the examiner focuses eyepiece 13 trying to achieve the brightest and best-focused image of the array of focal spots seen on the computer monitor. When the instrument is aligned with respect to the patient's eye and a best-focus image is obtained, the operator presses a key which commands the computer to acquire an image of the array of spots. During a measurement session, as many as ten successive images may be acquired for subsequent averaging to improve the signal/noise ratio of the data. The image analysis program carries out the following steps: 1) subtracts "background" light from the image, 2) determines the x & y coordinates (in pixels) of the centroid for each of the focal spots, 3) subtracts the x & y pixel coordinate values from a corresponding set of reference values (obtained from a calibration with a diffraction-limited reference lens), 4) multiplies the difference values (in pixel units) by a calibration factor which gives for each location in the pupil the components in the x and y directions of the wavefront slope error measured in radians. The components of the wavefront slope error, labeled Bx and By in the following sections, are the essential measurement data of the wavefront sensor.

4.2 Design of Aberration-Correcting Lens from Analysis of Wavefront Sensor Data

A purpose of the invention is to design modifications to an initially known lens surface, described by z(x,y), which will correct the eye's optical aberrations measured with wavefront sensors through that surface. In this section, the mathematical equations needed for this task, which leads to a new lens surface described by z'(x,y), are derived. The equations also are applied in an illustrative example. The mathematical formalism in this section is divided into the following parts: 1) description of original optical surface, 2) obtaining the directional derivatives of z'(x,y) from the wavefront sensor data, 3) obtaining a polynomial expansion representing z'(x,y) using the method of least squares, 4) illustrative example leading to z'(x,y), and 5) demonstration that z'(x,y) corrects the original aberrations. The following is a guide to the mathematical symbols (whether primed or not): a) x & y (and X & Y) are coordinates, b) n, R, Brms, $a_j$ & $b_j$ are scalars, c) z, δz/δx, δz/δy, MAG, α, β, λ, $g_j$, ERROR and CUT are functions of x & y, d) N, T, A, B, grad $g_j$ and grad z are three-dimensional vector functions of x & y, e) a & b are generalized vectors, and f) M and M⁻are generalized square matrices.

4.2.1 Original Optical Surface

By "original optical surface" is meant the anterior surface of either a contact lens placed on the cornea or, in the absence of a contact lens, the cornea itself. The index of refraction associated with the surface's denser side is n. The original optical surface is represented by z(x,y) which is the distance of the surface from various points in the x-y plane of the pupil. The unit vector perpendicular to the optical surface (called the normal vector N) has components in the x, y and z directions given by N=(Nx,Ny,Nz) where:

$$N_x = \frac{1}{MAG}\cdot\left[\frac{-\delta z(x,y)}{\delta x}\right],\ Ny = \frac{1}{MAG}\cdot\left[\frac{-\delta z(x,y)}{\delta y}\right],\ \text{and } N_z = \frac{1}{MAG} \tag{1}$$

$$\text{defining} \ldots\ MAG = \sqrt{1+\left[\frac{\delta z(x,y)}{\delta x}\right]^2+\left[\frac{\delta z(x,y)}{\delta y}\right]^2} \tag{2}$$

The x & y partial derivatives of the function describing the surface also can be expressed in terms of the components of the surface normal by rearranging the terms of Equa. 1.

$$\frac{\delta z(x,y)}{\delta x} = -\left[\frac{Nx}{Nz}\right] \text{ and } \frac{\delta z(x,y)}{\delta y} = -\left[\frac{Ny}{Nz}\right] \tag{3}$$

Figure 3:
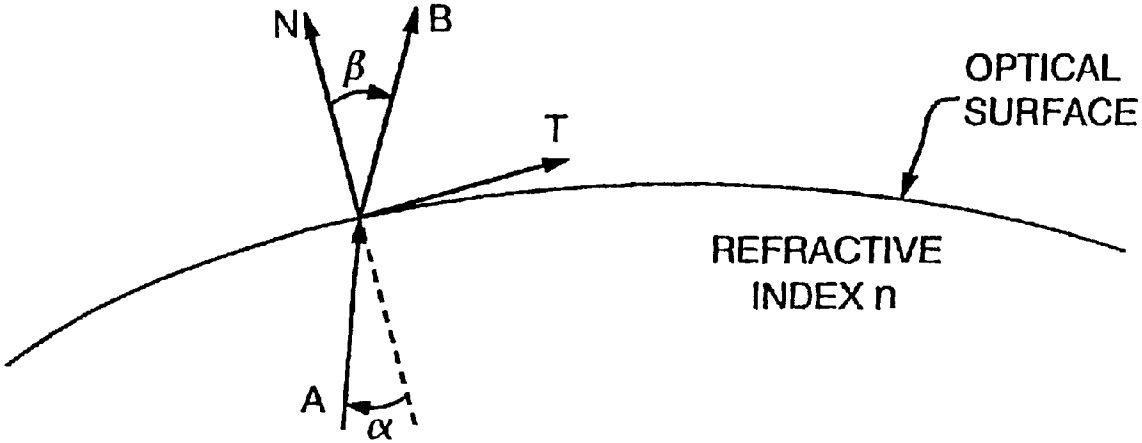

4.2.2 Obtaining the Partial Derivatives of the Surface Function which Describes the Aberration-Correcting Optical Surface The light rays, which emanate from the retinal "point source" formed by the wavefront sensor's projection system, emerge from the eye at the original optical surface which is described by z(x,y). Rays striking the surface from the denser side are described as A-vectors, and rays leaving the surface into air are described as B-vectors. Both A and B are vectors of unit length. Refer now to FIG. 3 to express the A and B vectors in terms of their components along N (surface normal) and T. Note that T is a unit vector tangent to the optical surface at the point of conjunction of (and coplanar with) rays A and B.

$$A \equiv \cos(\alpha)\cdot N + \sin(\alpha)\cdot T \tag{4}$$

$$B \equiv \cos(\beta)\cdot N + \sin(\beta)\cdot T \tag{5}$$

Next, substitute the expressions for A and B into n·A−B.

$$n\cdot A - B \equiv (n\cdot\cos(\alpha) - \cos(\beta))\cdot N + (n\cdot\sin)(\alpha)\cdot\sin(\beta))\cdot T \tag{6}$$

The second term vanishes due to Snell's Law of Refraction which is:

$$n\cdot\sin(\alpha) \equiv \sin(\beta) \tag{7}$$

From FIG. 3 and the definition of a vector cross product:

$$\sin(\beta) \equiv |N\cdot B| \tag{8}$$

The upright pair of lines in Equa. 8 indicates the magnitude of the vector enclosed by the pair.

Combining the results above, find the following equations:

$$\beta = \operatorname{asin}(|N \times B|) \tag{9}$$

$$\alpha = \operatorname{asin}\left[\frac{1}{n} \cdot \sin(\beta)\right] \tag{10}$$

$$A = \frac{1}{n} \cdot (\beta + \lambda \cdot N) \tag{11}$$

where by definition $$\lambda = n \cdot \cos(\alpha) - \cos(\beta) \tag{12}$$

Note that the B-vectors are known quantities representing the wavefront slopes as measured by the wavefront sensor. Using Equas. 9 through 12, the known quantities (B, N and n) determine the unknown quantities ($\beta$, $\alpha$, $\lambda$ and A).

Next, solutions for the A-vectors are used to find N', the unit normal to the aberration-correcting optical surface. This new surface causes the emerging B'-vectors to lie parallel to the z-axis. In vector form, B'=(0,0,1). The expression for N' is obtained by rearranging Equa. 11 to conform with this new situation.

$$N' = \frac{1}{\lambda'} \cdot (n \cdot A - B') \tag{13}$$

$$\text{where} \ \ldots \ \lambda' = |n \cdot A - B'| \tag{14}$$

Finally the following partial derivatives of the new aberration-correcting optical surface, described by z'(x,y), are obtained in terms of the components of unit vector N'=(Nx',Ny',Nz') by using Equa. 3 (only adapted to the new surface parameters):

$$\frac{\delta z'(x, y)}{\delta x} = -\left[\frac{Nx'}{Nz'}\right] \tag{15}$$

$$\frac{\delta z'(x, y)}{\delta y} = -\left[\frac{Ny'}{Nz'}\right] \tag{16}$$

4.2.3 Obtaining a Polynomial Expression to Represent z'(x,y)

The next problem is to find the new optical surface z'(x,y) from the partial derivatives expressed by Equa. 15 and 16, which are determined at discrete coordinate locations in the pupil plane, $[x_k, y_k]$, where the wavefront sensor data are obtained. Begin by expressing z'(x,y) as a polynomial consisting of linearly independent terms, g,(x,y).

$$z'(x, y) = \sum_j \alpha_j \cdot g_j(x, y) \tag{17}$$

The terms, $g_j(x,y)$ , can be almost any mathematical functions; however, they generally are restricted to products of powers of x and y, such as $x^3 \cdot y^2$, or sums and differences of such products. There is no necessity that the functions be orthogonal over the plane of the pupil as are, for example, Zernike polynomials over a circular domain. The coefficients, $a_j$, are constants which are determined by the methods derived below. Define "grad", the gradient, as a mathematical operator which transforms a scalar function, f(x,y) to a vector with components in the x and y directions that are, respectively, the partial derivatives of the function with respect to x and y.

$$\text{grad } f(x,y) = [\delta f(x,y)/\delta x, \ \delta f(x,y)/\delta y] \tag{18}$$

Applying this operator to both sides of Equa. 17, find $$\text{grad } z'(x, y) = \sum_j \alpha_j \cdot \text{grad } g_j(x, y) \tag{19}$$

To find the a-coefficients which provide the "best fit" to the data (i.e. the grad z' data expressed by Equa. 15 & 16), define the "ERROR" function as the sum of the squares of the differences between the grad z'(x,y) data from Equas. 15 & 16 (i.e. the left side of Equa. 19) and the estimated value of grad z'(x,y) (i.e. the right side of Equa. 19) for all the measurement points, designated by the index "k", in the x-y pupil plane.

$$\text{ERROR} = \sum_k \left[\sum_j \alpha_j \cdot \text{grad}[g_j] - \text{grad}(z')\right]^2 \tag{20}$$

For brevity sake, the notation for the variables (x,y) has been suppressed when writing the functions, $g_j(x,y)$ and z'(x,y), in Equa. 20. This abbreviated notation also is used in the equations which follow.

The "method of least squares" determines the a-coefficients by minimizing the ERROR function. This is done by differentiating ERROR with respect to each element $a_j$ and setting each resulting equation to zero: $\delta(\text{ERROR})/\delta a_j \equiv 0$. There are as many equations resulting from this process as there are terms in the expansion for z'(x,y) shown in Equa. 17. The resulting system of linear equations is written:

$$\sum_j \left[\sum_k [\text{grad}[g_i] \cdot \text{grad}[g_j]]\right] \cdot \alpha_j = \sum_k [\text{grad}[g_i] \cdot \text{grad}(z')] \tag{21}$$

Note that the sums over the index "k" imply a summation over all the $(x_k, y_k)$ coordinates in the pupil plane for the several g-functions and the grad z' values. Also, the products indicated in Equa. 21 are vector scalar products or, so-called, "dot products".

Defining matrix, M, and vector, b, in Equa. 22 & 23 below, Equa. 21 appears in the much simpler form which is shown by either Equa. 24 or Equa. 25. Note that M is a symmetric square matrix.

$$M_{i,j} = \sum_k [\text{grad}[g_i] \cdot \text{grad}[g_j]] \ \text{ so that } M_{i,j} = M_{j,i} \tag{22}$$

$$b_i = \sum_k [\text{grad}[g_i] \cdot \text{grad}(z')] \tag{23}$$

Thus, finding the a-coefficients is equivalent to solving the system of linear equations shown in Equa. 24 where matrix, M, and vector, b, are known quantities.

$$\sum_j M_{i,j} \cdot a_j = b_i \tag{24}$$

Using the conventions of standard matrix algebra, Equa. 24 may be written:

$$M \cdot a = b \tag{25}$$

The solution for vector, a, follows by using standard methods of linear algebra to obtain the inverse of matrix M which is designated by $M^{-1}$. Thus, the solution for vector, a, is shown as Equa. 26.

$$a \equiv M^{-1} \cdot b \tag{26}$$

The set of a-coefficients found from Equa. 26, using values of M (Equa. 22) and b (Equa. 23), is the final result. With the a-coefficients determined, the explicit "best fit" polynomial expansion for z'(x,y), shown by Equa. 17, is determined.

4.2.4 Illustrative Example

Consider, as an example, when the original optical surface is an acrylic contact lens with an index of refraction n=1.49, and with an anterior contour in the shape of a paraboloid described by $$z(x, y) = -\left[\frac{1}{2 \cdot R} \cdot [x^2 + y^2]\right].$$

The radius of curvature at the apex is 7.8 mm which is the constant R. All linear dimensions in this example, such as those described by x, y and z, are understood to be in millimeters.

The partial derivatives of z(x,y) are readily obtained. When these values are substituted into Equas. 1 and 2, the values for the components of the normal vector N as functions of x & y are readily obtained.

$$Nx = \frac{x}{\sqrt{R^2 + x^2 + y^2}} \tag{27}$$

$$Ny = \frac{y}{\sqrt{R^2 + x^2 + y^2}}$$

$$Nz = \frac{R}{\sqrt{R^2 + x^2 + y^2}}$$

In this example, measurements with the wavefront sensor are spaced 1 mm apart in the x and y directions within the domain of a circular pupil having an 8 mm diameter. There are 49 measurement sites. These data, which are the components in x & y of the emerging B-rays (i.e. Bx & By), are given by the two matrices shown below. The x-direction is to the right, and the y-direction is upward. Note that the values of Bx & By are multiplied by 1000 which makes the resulting directional units in milliradians.

$$1000 \cdot \tag{28}$$

$$Bx = \begin{bmatrix} 0 & 0 & 0 & 0 & 0.2 & 0 & 0 & 0 & 0 \\ 0 & 0 & 0.76 & 0.57 & 0.2 & -0.17 & -0.36 & 0 & 0 \\ 0 & 0.86 & 0.95 & 0.67 & 0.2 & -0.27 & -0.55 & -0.46 & 0 \\ 0 & 0.95 & 1.01 & 0.7 & 0.2 & -0.3 & -0.61 & -0.55 & 0 \\ 0.2 & 0.86 & 0.95 & 0.67 & 0.2 & -0.27 & -0.55 & -0.46 & 0.2 \\ 0 & 0.58 & 0.76 & 0.58 & 0.2 & -0.18 & -0.36 & -0.18 & 0 \\ 0 & 0.11 & 0.45 & 0.42 & 0.2 & -0.02 & -0.05 & 0.29 & 0 \\ 0 & 0 & 0.02 & 0.2 & 0.2 & 0.2 & 0.38 & 0 & 0 \\ 0 & 0 & 0 & 0 & 0.2 & 0 & 0 & 0 & 0 \end{bmatrix}$$

-continued $$1000 \cdot \tag{29}$$

$$By = \begin{bmatrix} 0 & 0 & 0 & 0 & -2.99 & 0 & 0 & 0 & 0 \\ 0 & 0 & -2.24 & -2.43 & -2.5 & -2.43 & -2.24 & 0 & 0 \\ 0 & -1.34 & -1.5 & -1.59 & -1.62 & -1.59 & -1.5 & -1.34 & 0 \\ 0 & -0.56 & -0.56 & -0.56 & -0.56 & -0.56 & -0.56 & -0.56 & 0 \\ 0 & 0.22 & 0.38 & 0.47 & 0.5 & 0.47 & 0.38 & 0.22 & 0 \\ 0 & 0.82 & 1.13 & 1.31 & 1.38 & 1.31 & 1.13 & 0.82 & 0 \\ 0 & 1.04 & 1.51 & 1.79 & 1.88 & 1.79 & 1.51 & 1.04 & 0 \\ 0 & 0 & 1.32 & 1.7 & 1.82 & 1.7 & 1.32 & 0 & 0 \\ 0 & 0 & 0 & 0 & 1.02 & 0 & 0 & 0 & 0 \end{bmatrix}$$

Figure 4:
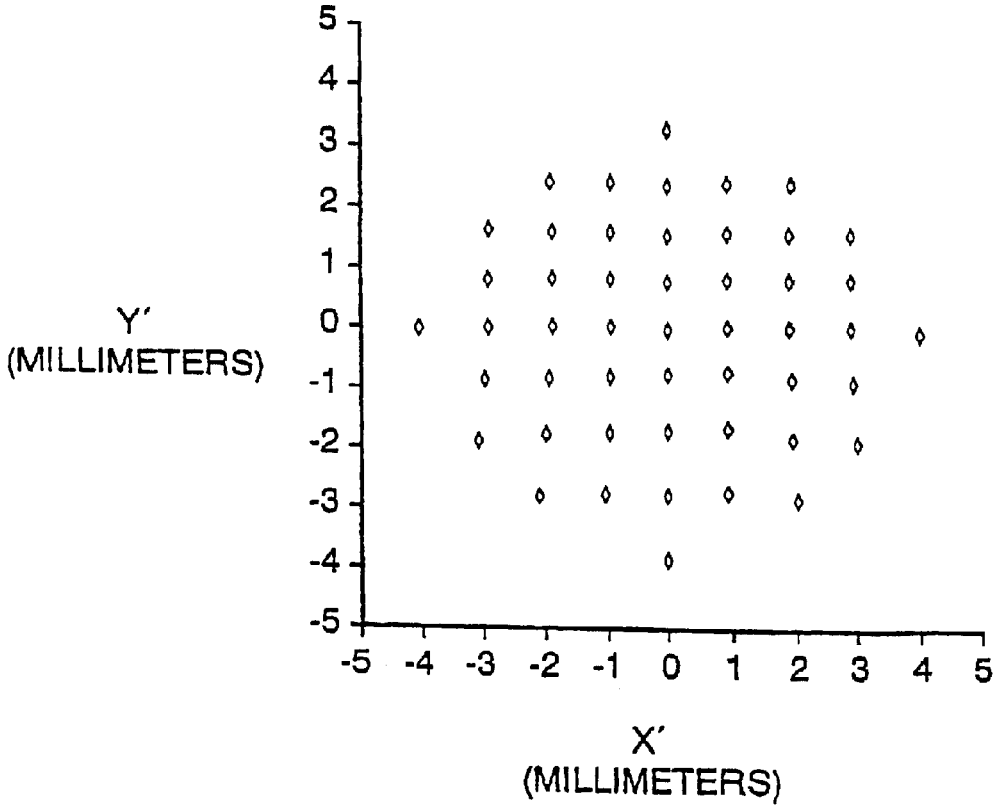

Bx & By represent the x & y directions of the rays emerging from the contact lens. The X and Y coordinates of the focal spots resulting from these rays, when imaged by the 1 mm spaced microlens array onto the wavefront sensor's measurement plane, are shifted somewhat from the intersection of the regular 1 mm spaced grid lines. The X & Y coordinate shifts are equal to the product of the focal length of the microlens array and the Bx and By values. In this example f=200 mm. The centroids of the focal spots of the wavefront sensor pattern are shown in FIG. 4.

A measure of the degree of collimation of all the B-rays is its root-mean-square value, labeled Brms. It is found by taking the square root of the average of all 49 values of $Bx^2+By^2$ as shown in Equas. 28 & 29. The value is Brms= 0.00148 radians.

Continuing with the methods to find the correcting surface, substitute the known numerical data (i.e. N summarized by Equa. 27, Bx and By given explicitly by Equas. 28 and 29, and n=1.49) into Equas. 9 through 12 in order to find the emerging A-rays. Then, Equas. 13 through 16 are used to find $\delta z'(x,y)/\delta x$ and $\delta z'(x,y)/\delta y$. Next, like Equa. 17, the following third order polynomial expression is used to represent z'(x,y).

$$z'(x,y) \equiv a_1 x + a_2 \cdot y + a_3 \cdot x^2 + a_4 \cdot x \cdot y + a_5 \cdot y^2 + \ldots + a_6 \cdot x^3 + a_7 \cdot x^2 \cdot y + a_8 \cdot x \cdot y^2 + a_9 \cdot y^3 \tag{30}$$

where $$g_1 \equiv x \quad g_2 \equiv y \quad g_3 \equiv x^2 \quad g_4 \equiv x \cdot y \quad g_5 \equiv y^5 \quad g_6 \equiv x^3 \quad g_7 \equiv x^2 \cdot y \quad g_8 \equiv x \cdot y^2 \quad g_9 \equiv y^3 \tag{31}$$

Finally, M, b and a are computed from Equas. 22, 23 and 26. The results of these calculations appear below. Note that the elements of the a-vector are the coefficients of the polynomial expression, Equa. 30, for z'(x,y). It is to be noted that, although the polynomial expression for z'(x,y) used in this example is only of order 3 for ease of illustration, the equations and methods of solution are easily extended to higher order polynomials. Programs to solve the resulting equations can be written using mathematical software available for use with personal computers. Of course, as the order of the polynomial increases, so too do the sizes of the M-matrix, and the b and a-vectors. For instance, associated with a polynominal of order 5 is a M-matrix having 20×20 elements, and b and a-vectors each having 20 elements.

$$M = \begin{bmatrix} 49 & 0 & 0 & 0 & 0 & 576 & 0 & 192 & 0 \\ 0 & 49 & 0 & 0 & 0 & 0 & 192 & 0 & 576 \\ 0 & 0 & 768 & 0 & 0 & 0 & 0 & 0 & 0 \\ 0 & 0 & 0 & 384 & 0 & 0 & 0 & 0 & 0 \\ 0 & 0 & 0 & 0 & 768 & 0 & 0 & 0 & 0 \\ 576 & 0 & 0 & 0 & 0 & 14040 & 0 & 1380 & 0 \\ 0 & 192 & 0 & 0 & 0 & 0 & 3400 & 0 & 1380 \\ 192 & 0 & 0 & 0 & 0 & 1380 & 0 & 3400 & 0 \\ 0 & 576 & 0 & 0 & 0 & 0 & 1380 & 0 & 14040 \end{bmatrix} \quad (32)$$

$$b = \begin{bmatrix} -0.02041 \\ -0.001126 \\ -49.09 \\ 0.000007021 \\ -48.69 \\ -0.2415 \\ 0.1101 \\ -0.08047 \\ 0.4015 \end{bmatrix} \text{ and } a = \begin{bmatrix} -0.0004123 \\ -0.001039 \\ -0.06392 \\ 0.00000001828 \\ -0.0634 \\ -0.0000002603 \\ 0.00006473 \\ -0.0000002798 \\ 0.00006487 \end{bmatrix} \quad (33)$$

The expression for z'(x,y) defined by Equa. 30 is determined only up to an arbitrary constant. When one considers that a machining operation generally is employed to reshape surface z(x,y) to the new modified surface z'(x,y) and that the machine has to be programmed to remove "positive" amounts of material, one realizes that the arbitrary constant has to be large enough to shift surface z'(x,y) so that, when shifted, its value can never be greater than z(x,y). For the example, z'(x,y) values are shifted in the negative z-direction by 0.011247 mm to satisfy this condition. The depth of cut to modify z(x,y) to the correcting surface is labelled CUT, and is expressed Equa. 34. Numerical values of 1000*CUT (in microns) at 1 mm spacings in the x & y directions are given in Equa. 35.

$$CUT(x,y) \equiv z(x, y) - (z'(x, y) - .011247) \quad (34)$$

$$1000 \cdot CUT = \begin{bmatrix} 0 & 0 & 0 & 0 & 0 & 0 & 0 & 0 & 0 \\ 0 & 0 & 4 & 5.5 & 6.3 & 6.3 & 5.6 & 0 & 0 \\ 0 & 6 & 7.9 & 9.3 & 10 & 10.1 & 9.6 & 8.5 & 0 \\ 0 & 8.1 & 9.7 & 10.9 & 11.5 & 11.7 & 11.4 & 10.6 & 0 \\ 6.7 & 8.4 & 9.7 & 10.7 & 11.2 & 11.5 & 11.4 & 10.9 & 10.1 \\ 0 & 7.3 & 8.3 & 9 & 9.6 & 9.9 & 9.9 & 9.8 & 0 \\ 0 & 5.2 & 5.9 & 6.4 & 6.9 & 7.2 & 7.5 & 7.7 & 0 \\ 0 & 0 & 2.8 & 3.2 & 3.6 & 4 & 4.5 & 0 & 0 \\ 0 & 0 & 0 & 0 & 0 & 0 & 0 & 0 & 0 \end{bmatrix} \quad (35)$$

4.2.5 Check that the New Surface Corrects Aberrations

In order to realize how well the new surface z'(x,y), described by the polynomial expression (Equa. 30) with the a-coefficients (Equa. 33), corrects the original optical aberrations, the following calculations are done: 1) find $\delta z'/\delta x$ and $\delta z/\delta y$ from Equa. 30 at all the measurement sites, and 2) use the values just found to find the x, y and z coordinates of N" from Equa. 1 & 2 where N" represents the normal to z'(x,y) [see Equa. 30]. Next rewrite Equa. 11 in the following form which takes into account the labelling for the new correcting surface:

$$B'' \equiv n \cdot A - \lambda'' \cdot N'' \quad (36)$$

B" represents the emerging rays after the surface has been corrected and is the parameter currently being sought. A, which is invariant with changes to the optical surface, is already known having been obtained previously by the methods described in the paragraph preceeding Equa. 30. Likewise N" is known, having been found by the methods outlined in the paragraph just above. At this stage, λ" is not yet determined; however, it is determined by the following methods.

First, from Equa. 9 find:

$$\beta'' = \text{asin}(|N'' \times B''|) \quad (37)$$

Since the vector product N"×N"=0, from Equa. 36 find that N"×B"=n*(N"×A). Therefore, Equa. 37 can be rewritten.

$$\beta'' = \text{asin}(|n^*(N'' \times A)|) \quad (38)$$

Since n, N" and A are now known parameters, Equa. 38 gives the solution for β".

Now that solutions for β" are found, the corresponding solutions for α" and λ" are found from modified forms of Equas. 10 & 12 which appear as . . .

$$\alpha'' = \text{asin}(\sin(\beta'')/n) \quad (39)$$

$$\lambda'' = n^* \cos(\alpha'') - \cos(\beta'') \quad (40)$$

B" can now be found from Equa. 36 by substituting the now known values for n, A, λ" and N". In Equas. 41 & 42, the x & y components of B", which are written as B"x and B"y, appear multiplied by 1000 which makes the resulting directional units in milliradians.

$$1000 \cdot B''x = \begin{bmatrix} 0 & 0 & 0 & 0 & 0 & 0 & 0 & 0 & 0 \\ 0 & 0 & -0.15 & 0.02 & 0 & -0.02 & 0.15 & 0 & 0 \\ 0 & -0.22 & 0.16 & 0.17 & 0 & -0.17 & -0.16 & 0.22 & 0 \\ 0 & 0.05 & 0.34 & 0.26 & 0 & -0.26 & -0.34 & -0.05 & 0 \\ -0.67 & 0.14 & 0.4 & 0.29 & 0 & -0.3 & -0.41 & -0.14 & 0.67 \\ 0 & 0.05 & 0.34 & 0.26 & 0 & -0.27 & -0.34 & -0.05 & 0 \\ 0 & -0.23 & 0.16 & 0.17 & 0 & -0.17 & -0.16 & 0.23 & 0 \\ 0 & 0 & -0.15 & 0.02 & 0 & -0.02 & 0.16 & 0 & 0 \\ 0 & 0 & 0 & 0 & 0 & 0 & 0 & 0 & 0 \end{bmatrix} \quad (41)$$

-continued $$1000 \cdot B''y = \begin{bmatrix} 0 & 0 & 0 & 0 & 0.63 & 0 & 0 & 0 & 0 \\ 0 & 0 & 0.22 & -0.04 & -0.13 & -0.05 & 0.21 & 0 & 0 \\ 0 & 0.15 & -0.15 & -0.33 & -0.39 & -0.33 & -0.15 & 0.14 & 0 \\ 0 & -0.01 & -0.16 & -0.26 & -0.29 & -0.26 & -0.17 & -0.01 & 0 \\ 0 & 0 & 0 & -0.01 & -0.01 & -0.01 & 0 & 0 & 0 \\ 0 & 0.02 & 0.16 & 0.25 & 0.28 & 0.25 & 0.16 & 0.02 & 0 \\ 0 & -0.14 & 0.15 & 0.33 & 0.39 & 0.33 & 0.16 & -0.14 & 0 \\ 0 & 0 & -0.22 & 0.05 & 0.14 & 0.05 & -0.21 & 0 & 0 \\ 0 & 0 & 0 & 0 & -0.65 & 0 & 0 & 0 & 0 \end{bmatrix} \quad (42)$$

A measure of the degree of collimation of all the B"-rays is its root-mean-square value, labeled B"rms. It is found by taking the square root of the average of all 49 values of $B''x^2+B''y^2$. The value of B"rms=0.00033 radians. That it is considerably less than the rms value for the original rays, which was Brms=0.00148 radians, demonstrates the success of the algorithms and methods.

With polynomial expansions for z'(x,y) having orders higher than 3 as in this current example, the corresponding size of B"rms is even less than the value given above. Furthermore, considering that 20/20 visual acuity implies resolving lines spaced 0.00029 radian apart (i.e. 1 minute of arc), the new correcting surface in this example is shown to improve visual acuity to very nearly 20/20.

Figure 5:
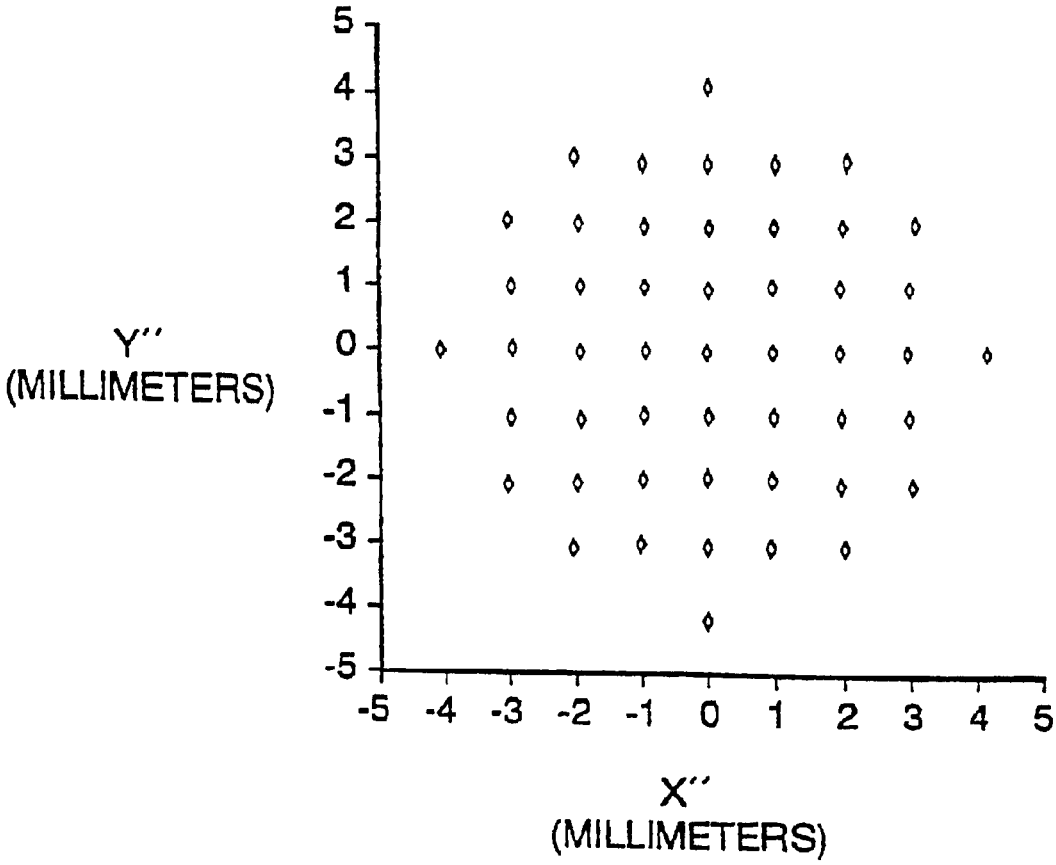

The centroids of the focal spots of the wavefront sensor pattern for the case of the corrected B"-rays from the new correcting surface z'(x,y) are shown in FIG. 5. When compared to FIG. 4, which shows the pattern for the original aberrating optical surface, FIG. 5 shows rays that are much better collimated.

Figure 6:
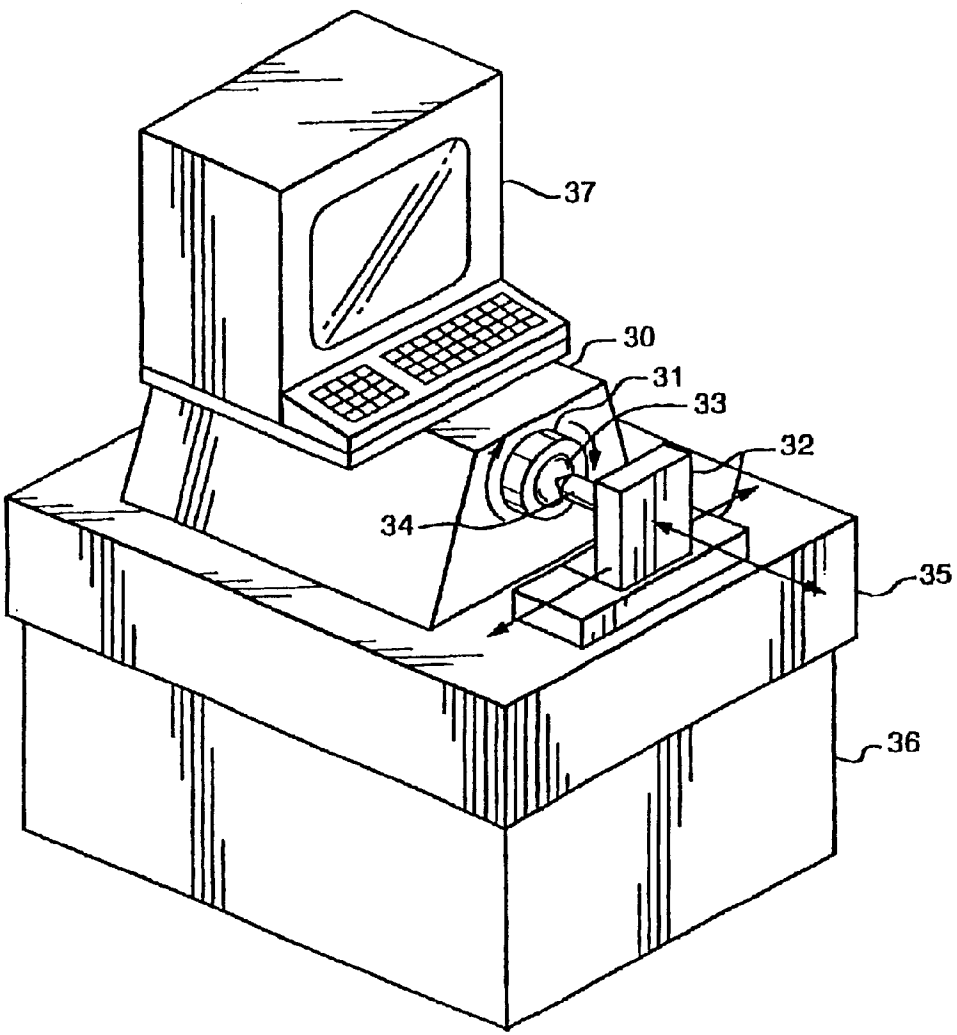

4.3 Fabrication of Aberration Correcting Surfaces on Lenses and Corneal Tissue 4.3.1 Diamond Point Machining Since the surface contours of aberration-correcting contact lenses described by z'(x,y) are more complex than the spherical or toroidal surfaces of conventional contact lenses, the position of a cutting tool needed to generate the z'(x,y) surfaces has to be controlled in a unique way. A programmable computer controlled single point diamond turning (SPDT) lathe, shown in FIG. 6, has been used to generate the surfaces of aberration-correcting contact lenses. The lathe 30 has two moving subassemblies: 1) a low vibration air bearing spindle 31, and 2) x-z positioning slides 32. Contact lens 33, which is held and centered on the end of spindle 31, is rotated by the spindle while a fine diamond tool 34 is moved by the positioning slides 32 with sub-micron resolution both perpendicular to (i.e. tool transverse scan in x-direction), and parallel to (i.e. tool cutting depth in z-direction) the direction of the spindle's axis. Smooth tool motion is achieved by the preferred means of using hydrostatic oil-bearing or air-bearing slideways. A preferred means for precise slide positioning is achieved by using computer controlled piezoelectric drivers or precise lead screw drivers (not shown). Since the machine must be completely free of both internal and external vibrations, both lathe 30 and x-z slides 32 are secured to a pneumatically isolated table top 35 which rests on granite base 36.

During lens machining, a computer 37 receives synchronous signals from spindle 31 and controls the movement of the x-z translation slides 32 along a programmed trajectory that is synchronized with the rotational position of the spindle. The motion of the x-translation slide (i.e. perpendicular to the spindle axis) generally is at a uniform speed as with an ordinary lathe. However, the requirement of forming a non-axially symmetric lens surface (i.e. z'(x,y) shape), when using a high speed lathe, requires a unique control method for positioning the z-translation slide (i.e. controls cutter movement parallel to the spindle axis and, consequently, the depth of cut on the lens surface which rotates rapidly with respect to the cutter). The z-translation slide must be rapidly and precisely located in accord with both the x-translation slide location, and the rotational position of the spindle. The preferred means of rapid and precise positioning of the z-translation slide is by the utilization of computer controlled piezoelectric drivers.

Finally, mounting the optical element firmly on a supporting block before placement on the end of the spindle is extremely important to avoid distorting the optical surface during machining. Care also must be taken to avoid distorting the lens blank when securing it to the supporting block; otherwise, the surface will warp after removing it from the block following final surfacing.

As an alternative to a precision lathe, custom contact lenses can also be machined by an x-y-z contour cutting machine. With a machine of this type, the lens is held stationary and figured by a cutting tool driven in a precise x-y raster scan while the depth of cut in the z-direction is controlled by a computer often with positional feedback provided by an interferometer. Such an x-y-z contour cutting machine is described by Plummer et al. at the 8th International Precision Engineering Seminar (1995), and published in those proceedings by the Journal of American Society of Precision Engineering, pp. 24–29.

4.3.2 Surfacing by Ablation using an Ultraviolet Laser

Laser ablation of corneal tissue currently is used to reshape the anterior corneal surface in order to correct near and farsightedness and astigmatism in the human eye. Laser tissue ablation also can be used to make more subtle corrections to the corneal surface than are now performed. Such corrections are needed to correct the eye's higher order optical aberrations. Therefore, laser surface ablation is a preferred method of contouring corneal tissue in order to correct the eye's higher order optical aberrations.

Also, as an alternative to machining optical plastic contact lenses with a fine diamond point tool, laser machining, similar to the laser ablation technique used to reshape the surface of the cornea, is also possible. It is likely that the most useful lasers for this purpose will prove to be those emitting ultra-violet light which ablate material away from surfaces, not by thermal heating or melting, but by rapid disruption of chemical bonds. Excimer lasers and solid state frequency-tripled (or frequency-quadrupled) Nd-YAG lasers are now proving to be useful both for machining plastics and ablating human tissue. These same lasers may be considered for precise surfacing operations needed for the fabrication of aberration correcting contact lenses or advanced refractive surgery.

4.4 Alternate Methods for Fabrication of Aberration Correcting Lenses

In addition to diamond point machining and laser ablation methods, there are other conceivable ways of fabricating an optical lens that can compensate for the eye's irregular optical aberrations. Any successful fabrication method must be capable of either precisely forming the lens surface to the required z'(x,y) shape, or meticulously varying the refractive index over the surface in order to bend the light rays to correct the aberrations. Described below are several alternate lens fabrication methods.

4.4.1 Mechanical Force Thermal Molding

If the lens is a thermoplastic, its surface may be formed to match that of a heated die. This method follows from the techniques used to form plastic parts by injection or compression molding. Since the desired topography of the lens surface generally is complex, the surface of the heated die is required to have a corresponding complex shape. When normally forming a plastic lens by the methods of injection or compression molding, the die which determines the shape of the lens is made of a single piece of metal and has a permanent surface shape. To form the customized and complex lens surfaces needed to correct the irregular aberrations of the human eye, it is necessary to construct and utilize dies with variable or "adaptive" surfaces. In the field known as "adaptive optics", such variable surfaces (anecdotally referred to as "rubber mirrors") have been formed and controlled using computer-derived input signals that drive electromechanical fingers which press against a deformable metal surface.

Such an arrangement, which is called here a variable segmented die, is shown in FIG. 7. The housing for the die 40 provides a number of channeled holes to hold a corresponding number of mechanical fingers 41 which are moved upwards or downwards in the die housing 40 by electronic drivers or actuators 42. Mechanical fingers 41 press against a continuous deformable metal surface 43 which contacts the thermoplastic lens surface and establishes its final shape. As an alternative to using a customized heated die with its surface formed by electromechanical fingers pressing in a controlled way against a deformable metal surface, an arrangement of close-packed, electronically actuated mechanical fingers without a deformable metal surface may be used. With this alternative arrangement, each mechanical finger in the array would press directly on the surface of the thermoplastic lens blank in order to form its surface as required.

4.4.2 Photolithography and Etching

A layer of photoresist is spun onto the glass or plastic lens substrate, and selectively exposed using either an optical scanner or an electron beam scanner. The exposure extent over regions of the surface of the photoresist is properly matched with the desired surface contour of the finished lens. The photoresist is developed chemically, thereby being selectively prepared for subsequent etching over those areas having previously received the most illumination. The surface of the glass or plastic lens substrate is then etched using reactive ion etching or chemically assisted ion-beam etching where the depth of the etch is determined by the extent of illumination during the previous exposure of the photoresist. It is noted that forms of PMMA (i.e. polymethyl methacrylate), which is a widely used optical plastic used for making contact lenses, are used as photoresists. Therefore, one can imagine tailoring the surface of a PMMA lens, in order to correct an eye's higher-order aberrations, directly without needing to use a separate photoresist layer over the lens substrate.

4.4.3 Thin Film Deposition:

There are various techniques now employed to add thin layers of various materials to the surfaces of glass and plastic optical lenses. The current purposes for applying such thin films to lenses are: 1) to limit the transmission of light, 2) to reduce surface reflections, and 3) to protect surfaces from scratching and abrasion. Some of the methods employed include dip coating, spin coating, evaporative coating, spraying, and ion sputtering. To modify these existing methods for the purpose of making a lens useful to correct the higher-order aberrations of the human eye will require refinements that allow the deposition of layers with thicknesses that vary selectively over the surface of the lens substrate in order to achieve the required z'(x,y) shape.

In addition to the methods now used to deposit thin films on optical surfaces, one can imagine other methods that may prove possibly more useful. Particularly useful could be a method of injecting from a fine nozzle or series of fine nozzles, which are in proximity to a surface, controlled amounts of transparent liquid materials that permanently bond when deposited on the surface. Scanning these controllable material-depositing nozzles over the surface of an optical substrate can result in building up on the optical substrate a custom surface contour that meets the requirements of correcting the higher-order optical aberrations of a subject's eye. Similar to what is conceived above is the operation of ink-jet devices used in computer printers.

4.4.4 Surface Chemistry Alteration:

Surfaces of flat glass disks have been implanted with certain ionic impurities that result in index of refraction changes that can vary radially from the center to the edge of the disk, or axially over the depth of the disk. Such methods are utilized in the fabrication of so-called "gradient index" optical elements, and flat disks are available commercially that behave as ordinary positive or negative lenses. Although plastic gradient index lenses have not yet been made, one can imagine altering the refractive index of a plastic subsurface by certain techniques. For example, the exposure of a plastic surface to ultraviolet light can alter the polymerization of subsurface macromolecules and, thereby, change the index of refraction in the subsurface region. For another example, the methods now used to imbibe dye molecules from solution into plastic surfaces in order to tint ophthalmic lenses may also be effective in changing the index of refraction in subsurface layers. In the future, it is conceivable that the methods of surface chemistry alteration, which are used now to fabricate "gradient index" optical elements, can be refined for both glass and plastic materials in order to make them useful in the fabrication of adaptive optical lenses for correcting the higher-order aberrations of the human eye.

REFERENCES CITED

U.S. Patent Documents:

U.S. Pat. No. 5,777,719 issued Jul. 7, 1998 to David R. Williams and Junzhong Liang entitled "Method and apparatus for improving vision and the resolution of retinal images"

Other References:

G Walsh, W N Charman, H C Howland. Objective technique for the determination of the monochromatic aberrations of the human eye. J. Opt. Soc. Am. A1, 987–992 (1984)

R H Webb, C M Penney, K P Thompson. Measurment of ocular wave-front distortion with a spatially resolved refractometer. Appl. Opt. 31, 3678–3686 (1992)

P Artal, J Santamaria, J Bescos. Retrieval of wave aberration of human eyes from actual point-spread-function data. J. Opt. Soc. Am. A5, 1201–1206 (1988)

P Magnante, B Fadden. Instrument for MTF measurements of cataractous eyes. Vision Science and its Applications-Opt Soc Am Meeting, 76–79 (1997)

R V Shack, B C Platt. Production and Use of Lenticular Hartmann Screen. J. Opt. Soc. Am. 61, 656 (1971)

J Liang, B Grimm, S Goetz, J F Billie. Objective measurements of wave aberrations of the human eye with the use of a Hartmann-Shack wave-front sensor. J. Opt. Soc. Am A11, 1949–1957 (1994)

D Malacara. Optical Shop Testing (Appendix 2). John Wiley and Sons, New York (1978)

I S Sokolnikoff, R M Redheffer. Mathematics of Physics and Modern Engineering (Chapter 9, Section 11). McGraw-Hill, New York (1958)

W T Plummer, J J Mader, J W Roblee, J Van Tassell. Precision Engineering at Polaroid. Reprint from 8$^{th}$ International Precision Engineering Seminar sponsored by J. Am. Soc. Prec. Eng., 24–29

What I claim as my invention is:

1. A method for correcting the optical aberrations beyond defocus and astigmatism of an eye fitted with an original contact lens having a known anterior surface shape by providing a modified or new contact lens which has its anterior surface reshaped from said original contact lens's anterior surface, comprising the steps of:

a) measuring said optical aberrations of an eye fitted with an original contact lens, b) performing a mathematical analysis of said eye's optical aberrations when fitted with original contact lens to determine said modified anterior contact lens surface shape, and c) fabricating said modified anterior contact lens surface by methods that remove, add or compress material or alter the surface chemistry.

2. A method as claimed in claim 1 wherein said measuring of the eye's optical aberrations comprises the sub-steps of:

i) optically projecting the image of a small point of incoherent light onto the macular region of the eye's retina, ii) optically conveying the image of the eye's pupil, through which light scattered back from the macular region emerges, onto a microlens array, iii) optically conveying the multiple spot images formed by said microlens array onto the image plane of a photo-electronic imaging device, iv) transforming by means of the photo-electronic imaging device the multiple spot images formed by said microlens array to an electronic signal which represents the images, v) conveying said electronic signal to a computer for data processing, vi) processing first the electronic signal with said computer in order to obtain the coordinate locations of the centroids of said multiple spot images formed by said microlens array, and vii) processing next said coordinate locations with said computer in order to obtain the slopes of optical rays emerging from the subject's pupil at said coordinate locations.

3. A method as claimed in claim 1 wherein said mathematical analysis comprises the sub-steps of:

i) determining mathematically the normal vectors of said original contact lens's anterior surface, ii) determining mathematically the directional derivatives of said modified or new contact lens's anterior surface using data of said normal vectors of original contact lens's anterior surface and data of said eye's optical aberrations, and iii) fitting mathematically by the method of least squares said directional derivatives to the corresponding directional derivatives of a polynomial expression that represents said modified or new contact lens's anterior surface.

4. A method as claimed in claim 1 wherein said step of fabricating said modified or new contact lens's anterior surface is chosen from the group of methods comprising diamond point machining, laser ablation, thermal molding, photo-lithographic etching, thin film deposition, and surface chemistry alteration.

5. A method for correcting the optical aberrations beyond defocus and astigmatism of an eye with an original anterior corneal surface of known shape by providing a modified anterior corneal surface shape, comprising the steps of:

a) measuring said eye's optical aberrations, b) performing a mathematical analysis of said eye's optical aberrations to determine said modified anterior corneal surface shape, c) fabricating said modified anterior corneal surface by laser ablation.

6. A method as claimed in claim 5 wherein said measuring of the eye's optical aberrations comprises the sub-steps of:

i) optically projecting the image of a small point of incoherent light onto the macular region of the eye's retina, ii) optically conveying the image of the eye's pupil, through which light scattered back from the macular region emerges, onto a microlens array, iii) optically conveying the multiple spot images formed by said microlens array onto the image plane of a photo-electronic imaging device, iv) transforming by means of the photo-electronic imaging device the multiple spot images formed by said microlens array to an electronic signal which represents the images, v) conveying said electronic signal to a computer for data processmg, vi) processing first the electronic signal with said computer in order to obtain the coordinate locations of the centroids of said multiple spot images formed by said microlens array, and vii) processing next said coordinate locations with said computer in order to obtain the slopes of optical rays emerging from the subject's pupil at said coordinate locations.

7. A method as claimed in claim 5 wherein said mathematical analysis comprises the sub-steps of:

i) determining mathematically the normal vectors of said original anterior corneal surface, ii) determining mathematically the directional derivatives of said modified anterior corneal surface using data of said normal vectors of original anterior corneal surface and data of said eye's optical aberrations, and iii) fitting mathematically by the method of least squares said directional derivatives to the corresponding directional derivatives of a polynomial expression that represents said modified anterior corneal surface.

8. An ophthalmic device for measuring the eye's optical aberrations either with or without a contact lens in place on the cornea, including;

a) an optical projection system for imaging a small point of light onto the macular region of the eye's retina with an improvement provided by use of an incoherent light source chosen from the group comprising laser diodes operated below threshold, light emitting diodes, arc and plasma sources, and incandescent filament lamps, b) an optical image acquisition system for conveying the image of the eye's pupil, through which light scattered back from the macular region emerges, onto a microlens array, c) a microlens array to form multiple spot images onto the image plane of a photo-electronic imaging device, d) a photo-electronic imaging device for transforming said multiple spot images formed by said microlens array to an electronic signal which represents the images, e) a computer for processing the electronic signal in order, first, to obtain the coordinate locations of the centroids of said multiple spot images formed by said microlens array and, second, to obtain the slopes of optical rays emerging from the subject's pupil at said coordinate locations, and f) an optical alignment system allowing the entering beam to be accurately centered with respect to the subject's pupil.

9. An ophthalmic device as claimed in claim 8 wherein said optical projection system includes an optical isolator consisting of a quarter-wave plate and polarizer.

10. An ophthalmic device as claimed in claim 8 wherein said optical projection system includes a field stop placed at a location that is optically conjugate to the eye's retina.

11. An ophthalmic device as claimed in claim 8 wherein said optical projection system includes both an optical isolator consisting of a quarter-wave plate and polarizer, and a field stop placed at a location that is optically conjugate to the eye's retina.

12. An ophthalmic device as claimed in claim 8 wherein said photo-electronic imaging device is chosen from the group comprising vidicons, charge-coupled devices, and charge-injection devices.

13. A device for thermally forming surfaces on thermoplastic contact lens blanks that correct eyes' optical aberrations beyond defocus and astigmatism consisting of a die with an adjustable surface shape (either continuous or discontinuous) formed by computer-controlled electromechanical actuators or electromechanical fingers which are known in the field of adaptive optics.

14. A lathe device for machining surfaces on contact lens blanks that correct eyes' optical aberrations beyond defocus and astigmatism consisting of a rotating spindle onto which a contact lens blank is fastened, translation slides for precisely positioning a diamond point cutting tool with respect to the surface of the contact lens blank, and a programmed computer that controls the movement of the translation slides synchronously with the rotational location of the spindle.

15. A contour cutting device for machining surfaces on contact lens blanks that correct eyes'optical aberrations beyond defocus and astigmatism consisting of a means for supporting and holding stationary a contact lens blank, translation slides for precisely positioning in three dimensions a diamond point cutting tool with respect to the surface of the contact lens blank, and a programmed computer that controls the movement of the translation slides.

*16. A method for correcting optical aberrations beyond defocus and astigmatism of an eye comprising:*

*a) fitting the eye with a first contact lens having a known anterior surface shape that is corrected for at least focus,*

*b) measuring the optical aberrations of the eye fitted with the first contact lens,*

*c) performing a mathematical analysis of the eye's optical aberrations when fitted with the first contact lens to determine a modified anterior contact lens surface shape, and*

*d) fabricating a second contact lens having the modified anterior contact lens surface.*

*17. A method as claimed in claim 16 performing the mathematical analysis to at least the eye's $4^{th}$ order optical aberrations of the eye when fitted with the first contact lens to determine the second contact lens surface shape, and the anterior surface of the second contact lens to have the modified anterior surface that corrects the eye to at least the $4^{th}$ order aberration.*

*18. A method as claimed in claim 17 wherein the measuring of the eye's optical aberrations comprises the sub-steps of:*

*i) optically projecting the image of a small point of incoherent light onto the macular region of the eye's retina,*

*ii) optically conveying the image of the eye's pupil, through which light scattered back from the macular region emerges, onto a microlens array,*

*iii) optically conveying the multiple spot images formed by the microlens array onto the image plane of a photo-electronic imaging device,*

*iv) transforming by means of the photo-electronic imaging device the multiple spot images formed by the microlens array to an electronic signal which represents the images,*

*v) conveying the electronic signal to a computer for data processing,*

*vi) processing first the electronic signal with the computer in order to obtain the coordinate locations of the centroids of the multiple spot images formed by the microlens array, and*

*vii) processing next the coordinate locations with the computer in order to obtain the slopes of optical rays emerging from the subject's pupil at the coordinate locations.*

*19. A method as claimed in claim 17 wherein the mathematical analysis comprises the sub-steps of:*

*i) determining mathematically the normal vectors of the first contact lens's anterior surface,*

*ii) determining mathematically the directional derivatives of the second contact lens's anterior surface using data of the normal vectors of the first contact lens's surface and data of the eye's optical aberrations, and*

*iii) fitting mathematically by the method of least squares the directional derivatives to the corresponding directional derivatives of a polynomial expression that represents the second contact lens's anterior surface.*

*20. A method as claimed in claim 1 wherein the original contact lens's anterior surface contour function $z(x,y)$ and the eye's optical aberrations, represented by optical rays emerging from the pupil given by vector function $B(x,y)$, are used to find the surface contour function $z'(x,y)$ of the modified or new contact lens by the following mathematical procedures:*

*a) $z'(x,y)$ is approximated by the sum of a series of linearly independent terms in x & y with each term labeled by an index j wherein each term, $a_j \cdot g_j(x,y)$, consists of an unknown constant coefficient $a_j$ and a known function $g_j(x,y)$ as shown in following Equation (1)*

$$z'(x, y) \equiv \sum_j a_j \cdot g_j(x, y) \quad (1)$$

b) *following Equation (2) is obtained by taking vector gradients of both sides of Equation (1) where grad z' (x,y) is a two-dimensional vector having components*

$$[\delta z' \ (x, y)/\delta x, \delta z' \ (x, y)/\delta y]$$

$$grad \ z'(x, y) = \sum_j a_j \cdot grad \ g_j(x, y) \quad (2)$$

c) *the normal vectors of the original contact lens's anterior surface, given by vector function N(x,y), are found by taking the vector gradient of z(x,y) and normalizing it to unity as shown in the following Equations (3A) to (3D)*

$$Nx \equiv \frac{1}{MAG} \cdot \frac{-\delta \ z(x, y)}{\delta \ x}, \quad (3A)$$

$$Ny \equiv \frac{1}{MAG} \cdot \frac{-\delta \ z(x, y)}{\delta \ y}, \quad (3B)$$

$$Nz \equiv \frac{1}{MAG} \quad (3C)$$

$$MAG \equiv [1+(\delta z(x,y)/\delta x)^2+(\delta z(x,y)/\delta y)^2]^{1/2} \quad (3D)$$

d) *the rays incident on the original contact lens coming from within the eye are given by vector function A(x,y) which is found by applying Snell's law of refraction at the air/lens interface which relates A(x,y) to known vector function B(x,y) representing the emerging rays, and vector function N(x,y) given by Equations (3A)–(3D),* e) *the normal vectors of the modified or new contact len's anterior surface, given by the vector function N', are found from the following Equation (4) where vector function B' is represented by unit vectors pointed along the positive z-axis, and n is the lens's refractive index*

$$N' \equiv \frac{(n \cdot A - B')}{|n \cdot A - B'|} \quad (4)$$

f) *the directional derivatives of the modified or new contact lens's anterior surface are obtained from the following Equation (5) using the components of vector function $N'=[N'_x, N'_y, N'_z]$ found from Equation (4)*

$$\frac{\delta \ z'}{\delta \ x} \equiv -\frac{N'_x}{N'_z} \ and \ \frac{\delta \ z'}{\delta \ y} \equiv -\frac{N'_y}{N'_z} \quad (5)$$

g) *apply the method of least squares to minimize the square the difference between the component values of grad z'(x,y) found from Equation (5) and the component values of grad z'(x,y) given by the approximation series, Equa. (2), in order to obtain matrix Equation (6)*

$$M \cdot a \equiv b \quad (6)$$

*where*

$$M_{(i,j)} \equiv \sum_{x,y} (grad \ g_i \cdot grad \ g_j) \ and \ b_i \equiv \sum_{x,y} (grad \ g_i \cdot grad \ z') \quad (7)$$

h) *obtain the inverse of matrix M, and then find the a-coefficients from matrix Equation (8)*

$$a \equiv M^{-1} \cdot b \quad (8)$$

i) *the a-coefficients determined from Equation (8) are used in Equation (1) which defines the modified or new contact lens's anterior surface, z' (x,y) when it is represented, for example, by a $5^{th}$ order Taylor series.*

*21. A methdo as claimed in claim 19 wherein the first Contact lens's anterior surface contour function z(x,y) and the eye's optical aberrations, represented by optical rays emerging from the pupil given by vector function B(x,y), are used to find the surface contour function z'(x−y) of the second contact lens by the following mathematical procedures:* a) *z' (x,y) is approximated by the sum of a series of linearly independent terms in x & y with each term labeled by an index j wherein each term, $a_j \cdot g_j(x,y)$, consists of an unknown constant coefficient $a_j$ and a known function $g_j(x,y)$ as shown in following Equation (1)*

$$z' \ (x, y) \equiv \sum_j a_j \cdot g_j(x, y) \quad (1)$$

b) *following Equation (2) is obtained by taking vector gradients of both sides of Equation (1) where grad z' (x,y) is a two-dimensional vector having components*

$$[\delta z' \ (x, y)/\delta x, \delta z' \ (x, y)/\delta y]$$

$$grad \ z'(x, y) = \sum_j a_j \cdot grad \ g_j(x, y) \quad (2)$$

c) *the normal vectors of the first contact lens's anterior surface, given by vector function N(x,y), are found by taking the vector gradient of z(x,y) and normalizing it to unity as shown in the following Equations (3A) to (3D)*

$$Nx \equiv \frac{1}{MAG} \cdot \frac{-\delta \ z(x, y)}{\delta \ x}, \quad (3A)$$

$$Ny \equiv \frac{1}{MAG} \cdot \frac{-\delta \ z(x, y)}{\delta \ y}, \quad (3B)$$

$$Nz \equiv \frac{1}{MAG} \quad (3C)$$

$$MAG \equiv [1+(\delta z(x,y)/\delta x)^2+(\delta z(x,y)/\delta y)^2]^{1/2} \quad (3D)$$

d) *the rays incident on the first contact lens coming from within the eye are given by vector function A(x,y) which is found by applying Snell's law of refraction at the air/lens interface which relates A(x,y) to known vector function B(x,y) representing the emerging rays, and vector function N(x,y) given by Equations (3A)–(3B),* e) *the normal vectors of the second contact lens's anterior surface, given by the vector function N', are found from*

*the following Equation (4) where vector function B′ is represented by unit vectors pointing along the positive z-axis, and n is the lens's refractive index*

$$N' = \frac{(n \cdot A - B')}{|n \cdot A - B'|} \tag{4}$$

*f) the directional derivatives of the second contact lens's anterior surface are obtained from the following Equation (5) using the components of vector function N′= [N′x,N′y,N′z] found from Equation (4)*

$$\frac{\delta z'}{\delta x} \equiv -\frac{N'_x}{N'_z} \text{ and } \frac{\delta z'}{\delta y} \equiv -\frac{N'_y}{N'_z} \tag{5}$$

*g) apply the method of at least squares to minimize the square the difference between the component values of grad z′ (x,y) found from Equation (5) and the component values of grad z′ (x,y) given by the approximation series, Equa. (2), in order to obtain matrix Equation (6)*

$$M \cdot a \equiv b \tag{6}$$

*where*

$$M_{(i,j)} \equiv \sum_{x,y} (grad\ g_i \cdot grad\ g_j) \text{ and } b_i = \sum_{x,y} (grad\ g_i \cdot grad\ z') \tag{7}$$

*h) obtain the inverse of matrix M, and then find the a-coefficient from matrix Equation (8)*

$$a \equiv M^{-1} \cdot b \tag{8}$$

*i) the a-coefficients determined from Equation (8) are used in Equation (1) which defines the second contact lens's anterior surface, z′ (x,y) when it is represented, for example, by a 5th order Taylor series.*

*22. A method as claimed in claim 5 wherein the original cornea's anterior surface contour function z(x,y) and the eye's optical aberrations, represented by optical rays emerging from the pupil given by vector function B(x,y), are used to find the surface contour function z′(x,y) of the modified cornea by the following mathematical procedures:*

*a) z′ (x,y) is approximated by the sum of a series of linearly independent terms in x & y with each term labeled by an index j wherein each term, $a_j \cdot g_j(x,y)$, consists of an unknown constant coefficient $a_j$ and a known function $g_j(x,y)$ as shown in following Equation (1)*

$$z'(x, y) \equiv \sum_j a_j \cdot g_j(x, y) \tag{1}$$

*b) following Equation (2) is obtained by taking vector gradients of both sides of Equation (1) where grad z′ (x,y) is a two-dimensional vector having components*

$$[\delta z'(x, y)/\delta x, \delta z'(x, y)/\delta y]$$

$$grad\ z'(x, y) = \sum_j a_j \cdot grad\ g_j(x, y) \tag{2}$$

*c) the normal vectors of the original cornea's anterior surface, given by vector function N(x,y), are found by taking the vector gradient of z(x,y) and normalizing it to unity as shown in the following Equations (3A) to (3D)*

$$Nx \equiv \frac{1}{MAG} \cdot \frac{-\delta z(x, y)}{\delta x}, \tag{3A}$$

$$Ny \equiv \frac{1}{MAG} \cdot \frac{-\delta z(x, y)}{\delta y}, \tag{3B}$$

$$Nz \equiv \frac{1}{MAG} \tag{3C}$$

$$MAG \equiv [1 + (\delta z(x,y)/\delta x)^2 + (\delta z(x,y)/\delta y)^2]^{1/2} \tag{30}$$

*d) the rays incident on the original cornea coming from within the eye are given by vector function A(x,y) which is found by applying Snell's law of reflection at the air/cornea interface which relates A(x,y) to known vector function B(x,y) representing the emerging rays, and vector function N(x,y) given by Equations (3A)–(3B),*

*e) the normal vectors of the modified cornea's anterior surface, given by the vector function N′, are found from the following Equation (4) where vector function B′ is represented by unit vectors pointing along the positive z-axis, and n is the cornea's refractive index*

$$N' \equiv \frac{(n \cdot A - B')}{|n \cdot A - B'|} \tag{4}$$

*f) the directional derivatives of the modified cornea's anterior surface are obtained from the following Equation (5) using the components of vector function N′= [N′x, N′y, N′z] found from Equation (4)*

$$\frac{\delta z'}{\delta x} \equiv -\frac{N'_x}{N'_z} \text{ and } \frac{\delta z'}{\delta y} \equiv -\frac{N'_y}{N'_z} \tag{5}$$

*g) apply the method of least squares to minimize the square the difference between the component values of grad z′(x,y) found the Equation (5) and the component values of grad z′ (x,y) given by the approximation series, Equa. (2), in order to obtain matrix Equation (6)*

$$M \cdot a \equiv b \tag{6}$$

*where*

$$M_{(i,j)} \equiv \sum_{x,y} (grad\ g_i \cdot grad\ g_j) \text{ and } b_i = \sum_{x,y} (grad\ g_i \cdot grad\ z') \tag{7}$$

*h) obtain the inverse of matrix M, and then find the a-coefficients from matrix Equation (8)*

$$a \equiv M^{-1} \cdot b$$

*i) the a-coefficient determined from Equation (8) are used in Equation (1) which defines the modified cornea's anterior surface, z′ (x,y) when it is represented, for example, by a 5th order Taylor series.*

23. A contact lens comprising an anterior surface which is fabricated to correct the optical aberration to at least $4^{th}$ order of a person's eye.

24. The contact lens of claim 23 wherein the measuring of the eye's optical aberrations is by steps of:

(i) optically projecting the image of a small point of incoherent light onto the macular region of the eye's retina, (ii) optically conveying the image of the eye's pupil, through which light scattered back from the macular region emerges onto a microlens array, (iii) optically conveying the multiple spot images formed by the microlens array onto the image plane of a photo-electronic imaging device, (iv) transforming by means of the photo-electronic imaging device the multiple spot images formed by the microlens array to an electronic signal which represents the images;

(v) conveying the electronic signal to a computer for data processing, (vi) processing first the electronic signal with the computer in order to obtain the coordinate locations of the centroids of the multiple spot images formed by the microlens array, and (vii) processing next the coordinate locations with the computer in order to obtain the slopes of optical rays emerging from the subject's pupil at the coordinate locations.

25. The contact lens of claim 23 wherein the mathematical analysis comprises the sub-steps of:

(a) determining mathematically the normal vectors of a first contact lens anterior surface;

(b) determining mathematically the directional derivatives of the a second contact lens anterior surface using data of the normal vectors of the first contact lens anterior surface and data of the eye's optical aberrations; and (c) fitting mathematically by the method of least squares the directional derivatives to the corresponding directional derivatives of a polynomial expression that represents the second contact lens anterior surface.

26. The contact lens of claim 23 wherein the first contact lens anterior surface contour function $z(x,y)$ and the eye's optical aberrations, represented by optical rays emerging from the pupil given by vector function $B(x,y)$, are used to find the surface contour function $z'(x,y)$ of the second contact lens by the following mathematical procedures:

(a) $z'(x,y)$ is approximated by the sum of a series of linearly independent terms in x & y with each term labeled by an index j wherein each term, $a_j \cdot g_j(x,y)$, consists of an unknown constant coefficient $a_j$ and a known function $g_j(x,y)$ as shown in following Equation (1)

$$z'(x, y) \equiv \sum_j a_j \cdot g_j(x, y) \tag{1}$$

b) following Equation (2) is obtained by taking vector gradients of both sides of Equation (1) where grad $z'(x,y)$ is a two-dimensional vector having components $[\delta z'(x,y)/\delta x,\ \delta z'(x,y)/\delta y]$ $$grad\ z'(x, y) = \sum_j a_j \cdot grad\ g_j(x, y) \tag{2}$$

c) the normal vectors of the first contact lens's anterior surface, given by vector function $N(x,y)$, are found by taking the vector gradient of $z(x,y)$ and normalizing it to unity as shown in the following Equations (3A) to (3D)

$$Nx \equiv \frac{1}{MAG} \cdot \frac{-\delta\ z(x, y)}{\delta\ x}, \tag{3A}$$

$$Ny \equiv \frac{1}{MAG} \cdot \frac{-\delta\ z(x, y)}{\delta\ y}, \tag{3B}$$

$$Nz \equiv \frac{1}{MAG} \tag{3C}$$

$$MAG \equiv [1+(\delta z(x,y)/\delta x)^2+(\delta z(x,y)/\delta y)^2]^{1/2} \tag{3D}$$

d) the rays incident on the first contact lens coming from within the eye are given by vector function $A(x,y)$ which is found by applying Snell's law of refraction at the air/lens interface which relates $A(x,y)$ to known vector function $B(x,y)$ representing the emerging rays, and vector function $N(x,y)$ given by Equations (3A)–(3B), e) the normal vectors of the second contact lens's anterior surface, given by the vector function $N'$, are found from the following Equation (4) where vector function $B'$ is represented by unit vectors pointing along the positive z-axis, and n is the lens's (or cornea's) refractive index $$N' \equiv \frac{(n \cdot A - B')}{|n \cdot A - B'|} \tag{4}$$

f) the directional derivatives of the second contact lens's anterior surface are obtained from the following Equation (5) using the components of vector function $N' = [N'_x, N'_y, N'_z]$ found from Equation (4)

$$\frac{\delta\ z'}{\delta\ x} \equiv -\frac{N'_x}{N'_z} \quad and \quad \frac{\delta\ z'}{\delta\ y} \equiv -\frac{N'_y}{N'_z} \tag{5}$$

g) apply the method of least squares to minimize the square the difference between the component values of grad $z'(x,y)$ found from Equation (5) and the component values of grad $z'(x,y)$ given by the approximation series, Equa. (2), in order to obtain matrix Equation (6)

$$M \cdot a \equiv b \tag{6}$$

where $$M_{(i,j)} \equiv \sum_{x,y} (grad\ g_i \cdot grad\ g_j) \quad and \quad b_i \equiv \sum_{x,y} (grad\ g_i \cdot grad\ z') \tag{7}$$

h) obtain the inverse of matrix M, and then find the a-coefficients from matrix Equation (8)

$$a \equiv M^{-} \cdot b \tag{8}$$

i) the a-coefficients determined from Equation (8) are used in Equation (1) which defines the second contact lens's anterior surface, $z'(x,y)$ when it is represented, for example, by a $5^{th}$ order Taylor series.

* * * * *